United States Patent [19]

Maier

[11] Patent Number: 4,802,360

[45] Date of Patent: Feb. 7, 1989

[54] VIBRATING SPOOL DENSITOMETER IMMUNE TO CABLING EFFECTS

[75] Inventor: Lawrence C. Maier, New Haven, Vt.

[73] Assignee: Simmonds Precision Products, Inc., Tarrytown, N.Y.

[21] Appl. No.: 31,850

[22] Filed: Mar. 27, 1987

[51] Int. Cl.[4] ............................................. G01N 9/00
[52] U.S. Cl. ................................................... 73/32 A
[58] Field of Search .................... 73/32 A, 30; 331/65

[56] References Cited

U.S. PATENT DOCUMENTS

| | | |
|---|---|---|
| 4,215,566 | 8/1980 | Ghahramani ........................ 73/32 A |
| 4,282,742 | 8/1981 | Kalotay et al. ...................... 73/32 A |

Primary Examiner—John Chapman
Attorney, Agent, or Firm—Cushman, Darby & Cushman

[57] ABSTRACT

Apparatus for use with a densitometer having a probe with an output and a probe driver for driving the probe includes a loop circuit coupled between the probe output and the probe driver. An amplifying circuit is coupled in the loop circuit to amplify the signal provided by the probe. A phase/gain control device is also coupled in the loop circuit between the amplifying device and the probe driver. The phase/gain control device controls the loop circuit to provide a loop gain of at least one and a substantially zero degree phase shift between the probe driver and the probe output signal. The amplifying device includes an op-amp which is preferably coupled to a shielded cable carrying the probe output signal. The shield conductor and one input of the op-amp are held at ground potential, and the op-amp acts to hold the center conductor at ground potential also. With the center conductor held at ground potential, the output signal from the probe varies with current, not voltage. A resistance in the feedback path of the op-amp converts current changes to voltage changes proportional to the output signal of the probe. Since the center conductor of the shielded cable varies in current only, the output signal from the probe is insensitive to cable length, cable loading, and cable capacitance.

19 Claims, 2 Drawing Sheets

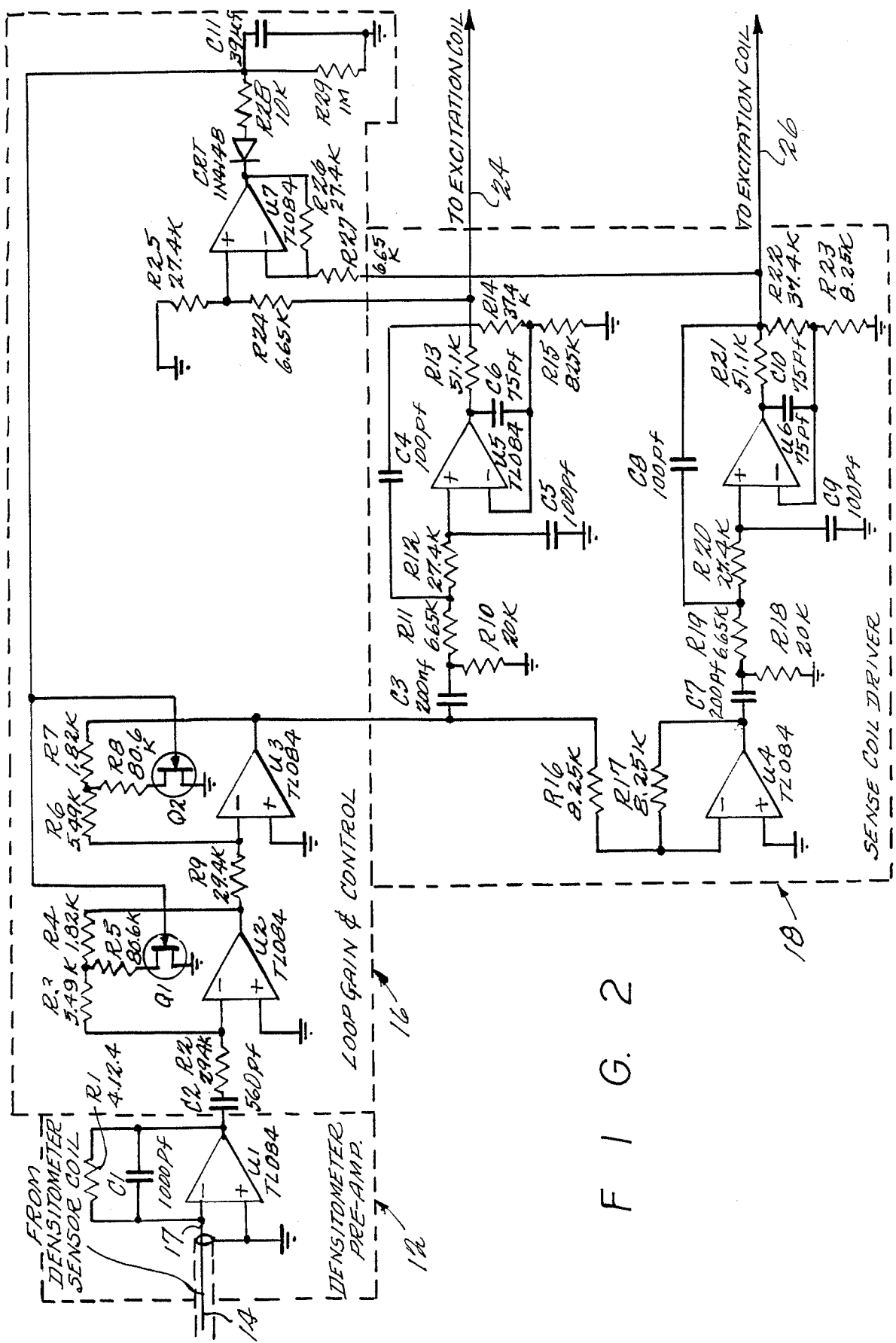
F I G. 2

VIBRATING SPOOL DENSITOMETER IMMUNE TO CABLING EFFECTS

BACKGROUND OF THE INVENTION

The present invention relates to a vibrating spool density sensor used to determine the density of a fluid in a tank, for example, an aircraft fuel tank. More particularly, the present invention relates to a vibrating spool densitometer having an inut signal which is dependent only upon the fluid in which the sensor is immersed, and is not dependent upon the length, shielding, or capacitive loading of the cable which connects the densitometer to an indicator.

Vibrating spool densitometers are known for determining the density of a fluid in a tank. Such densitometers are particularly useful in an aircraft fuel tank for providing fuel status to the pilot. Basically, a vibrating spool densitometer comprises a probe inserted into the fuel tank, and an interface for coupling the probe output signal to a processor which provides an appropriate indication to the pilot. The probe includes a vibrating vane or spool which is stimulated by a spool driver to vibrate at resonance. A pickup coil or crystal picks up vibrations from the tank and provides an output signal containing information about the density of the fluid in the tank.

In the prior art, an interface unit for the vibrating spool density sensor was provided near the fuel tank to receive the probe output signal and condition it for transmittal to a processor. However, such interface units are extremely sensitive to cable capacitance which thus precludes the use of protective shielding cable. Furthermore, the sensitivity to cable capacitance required the interface unit to be located within 20 feet of the density sensor. Typically, a separate electronic interface unit was mounted near the fuel tank containing the sensor. On a large aircraft, as many as six fuel tanks were used, thus requiring six electronic interface units. The number and location of such interface units obviously increased the aircraft weight and diminished reliability.

Such prior art densitometers are disclosed, inter alia, in U.S. Pat. No. 4,546,641 to Nguyen. Since the output of sensor 14 therein comprises two separate lead lines, preamplifier 16 must be located near the fuel tank.

Likewise, a known densitometer is disclosed in U.S. Pat. No. 4,495,818 to Ikeda et al. In FIG. 5, Ikeda discloses an electrical circuit for vibrating the vibrator 1 at its resonant frequency. Amplifier U4 is used to rotate the phase of the output signal from the limiter to satisfy the condition for self-oscillation. However, the device of Ikeda et al is directed to the physical construction of the pressure transducer, and also must include an interface unit coupled near the fuel tank.

Finally, U.S. Pat. No. 4,215,566 to Ghahramani discloses a vibration densitometer having a magnetostrictive drive with a coil and a crystal pickup. A loop circuit including an driver amplifier provides the coil with a voltage twice that ordinarily provided. However, Ghahramani also requires an interface unit coupled in proximity to the fuel tank.

Such known vibrating densitometer interface units were required to provide the oscillator with components necessary for generation of a frequency for processing by an appropriate fuel tank signal conditioner. The remote signal conditioner was required because of the characteristics of the densitometer, the interface electronics, and the interconnecting cable. Thus, known vibration densitometers require additional electronic units, thereby increasing the cost, complexity, weight, and reliability risk of the aircraft.

SUMMARY OF THE INVENTION

The present invention overcomes disadvantages of known vibration densitometers by eliminating the need for interface units located at each fuel tank. The present invention provides a means of signal conditioning a vibrating spool densitometer signal in such a fashion that the vibration frequency of the densitometer is dependent only upon the fluid in which the sensor is immersed, and is not dependent upon the length, shielding, or capacitive loading of the interconnection cable. Therefore, the interconnection cable may now be shielded. This further protects the system from influences of high energy fields, for example, RF interference.

Since the output signal of the vibration densitometer is now independent of the length of cabling, the signal conditioning circuitry which transmits the probe output signal to the appropriate processor may now be located at any desired location in the aircraft, thus eliminating extra electronic packages. In fact, the signal conditioning circuitry may now be located at the processor location itself.

A vibrating spool densitometer according to the present invention includes a loop circuit coupled between the probe output and coil driver. A densitometer preamplifier and cable compensation circuit is coupled in the loop circuit and amplifies the output signal of the densitometer probe such that the signal carried on the probe output wire is current-varying and not voltage-varying. A loop gain and control circuit is coupled in the loop circuit between the densitometer preamplifier and a coil driver. The loop gain and control device controls the loop circuit to provide a loop gain of at least one, and a substantially zero degree phase shift between the probe output signal and the probe driver output signal.

Preferably, the probe output is connected to the densitometer preamplifier cable compensation circuit through a shielded cable which is immune to high energy fields.

BRIEF DESCRIPTION OF THE DRAWINGS

The advantageous structure and features of the present invention will become more apparent from the following detailed description of the preferred exemplary embodiment, when taken together with the attached drawings, in which:

FIG. 2 is a detailed schematic of the preferred embodiment.

DETAILED DESCRIPTION OF THE PRESENTLY PREFERRED EXEMPLARY EMBODIMENT

Figure 1:
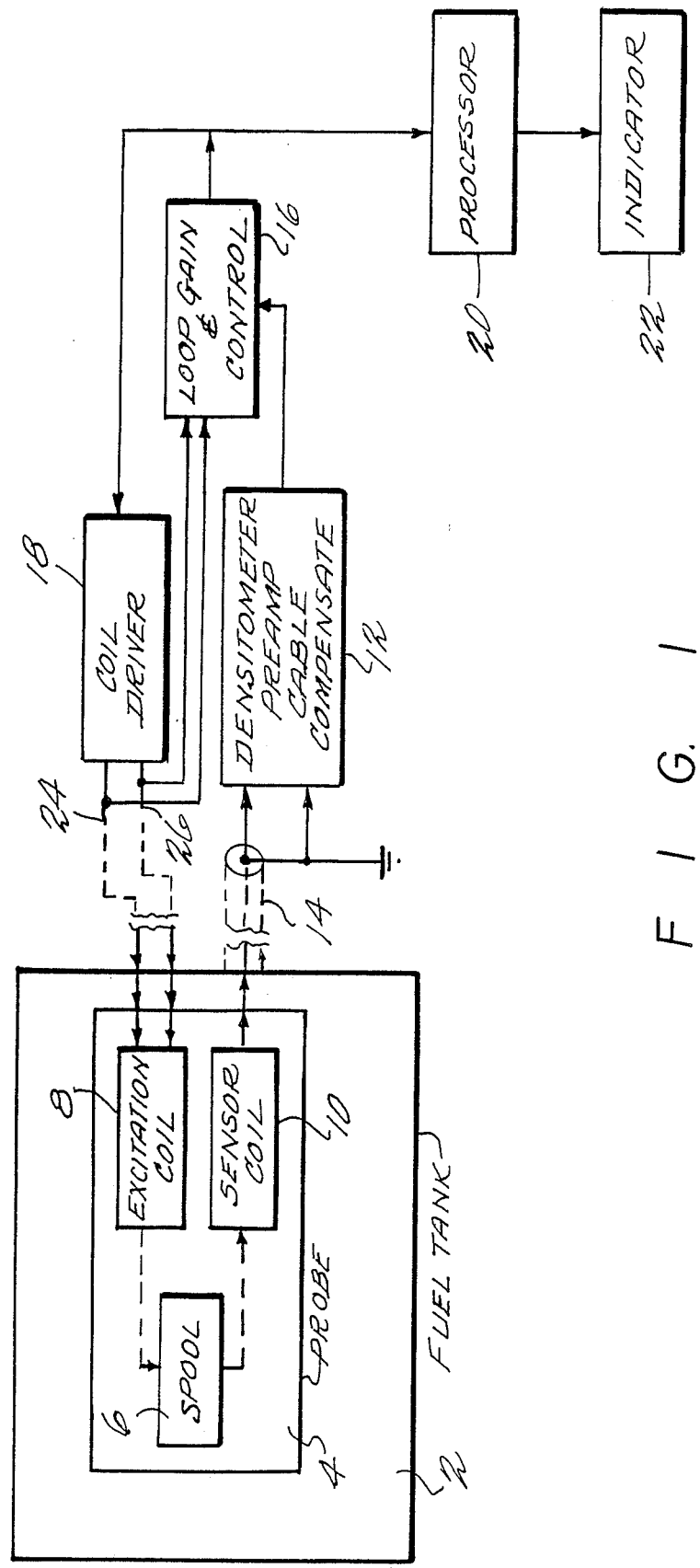
FIG. 1 is a block diagram of a preferred embodiment.

In brief, the present invention allows a densitometer sensor to be located in a fuel tank with no active electronics associated with the densitometer in the tank hardware. The required signal conditioning for the densitometer sensor is located in an electronics package which does not have to be located near the fuel tank. The present invention is designed with a view toward keeping the probe output signal immune to cabling effects. The present invention presents no problem wiring coaxial or shielded cable to interconnect the density sensor with the appropriate signal conditioning electronics package. The design of the electronics according to the present invention also limits tank energy to less than 0.1 microjoules, and the current to less than 10 milliamperes. These current and energy levels are intrinsically safe.

The electronics package for the densitometer may be supplied with appropriate driving voltage (typically 28 VDC for an aircraft) from the appropriate fuel quantity channel. Internal circuitry sustains densitometer spool vibration (which relates to fuel density) and the sine wave output of the electronics package is sent to a processor unit. Calibration constants for the densitometer may be carried as resistors in a potted area behind the densitometer sensor. The resistor values are read by a processing unit, so that a densitometer frequency output can be converted directly into fuel density. The calibration values are carried on each density sensor; therefore, the densitometer may be replaced as required without affecting system calibration and without any calibration data entry required by aircraft maintenance personnel. There is no need to do anything to the electronics package if a densitometer is replaced, and no need to do anything to the densitometer if the electronics package is replaced.

The present invention also allows the signal conditioning circuitry for the densitometer to be placed in the same processor electronics package that measures the fuel tank quantity, thus eliminating the additional interface electronics package required by known vibration densitometers.

Since the present invention provides for densitometer signal conditioning which is not sensitive to cabling effects, a number of advantages accure, such as increased system reliability, easier installation, lower weight, and lower cost.

In FIG. 1, fuel tank 2 includes a probe 4 which may comprise a vibrating spool 6 driven by an excitation device, for example an excitation coil 8. Sensor coil 10 picks up spool vibrations and provides a probe output signal which is outputted from fuel tank 2. A variety of alternative sensors may be provided, such as a crystal or magnetic sensor.

The probe output signal from sensor coil 10 is provided to a densitometer preamplifier cable compensation circuit 12 via cabling 14. It is particularly preferred that cable 14 comprise a coaxial cable, or any other known shielded cabling suitable for such use. The shielding conductor of cable 14 is coupled to ground, for reasons described later herein. The shielded conductor is also coupled to the densitometer preamplifier circuit 12, as is the signal conductor of cable 14.

Densitometer preamplifier 12 is an important part of the present invention. It allows the signal from the sensor coil 10 of a vibrating spool densitometer to be amplified with a phase shift independent of the length or capacitance loading of the cable connecting the densitometer to the densitometer preamplifier 12. In order for the sensor to operate properly, the phase of the signal from the sensor coil 10 must be carefully controlled. Any uncontrolled phase shift will cause the sensor to stop vibrating, resulting in a loss of signal. Previous methods of signal conditioning required the sensor to be located close to the electronics signal conditioning package to avoid such phase shifts. Densitometer preamplifier 12 makes the system relatively insensitive to cabling effects, thus allowing the densitometer preamplifier 12 to be located in any convenient location.

The amplified signal from densitometer preamplifier 12 is applied to a loop gain and control circuit 16. Loop gain and control circuit 16 provides an input to coil driver 18 and also samples the output signals from coil driver 18.

Loop gain and control circuit 16 is configured to ensure a substantially zero degree phase shift between the sensor coil output signal and the coil driver output signal. The densitometer is a resonant element sensor. At the frequencies of interest, the sensor has a gain peak and a phase of zero degrees between the input (coil driver 18) and the output (sensor coil 10). In order to sustain oscillation of the vane or spool at the resonant frequency, loop gain and control circuit 16 must provide a loop gain of at least one, and a phase shift of zero degrees. The conditions required to sustain oscillation are well known to anyone versed in the art. Loop gain and control section 16 monitors the outputs of coil driver 18 and adjusts the loop gain such that spool oscillations are just sustained. Any phase errors in the loop circuit are detected and corrected beforehand by making part substitutions in the loop gain and control circuit, as described later herein.

The loop gain and control circuit 16 provides an output signal which corresponds to the density of the fuel in fuel tank 2. This output signal may be provided to a processor 20 which may provide a fuel density indication on indicator 22. As above indicated, the output signal from loop gain and control circuit 16 is also applied to coil driver 18 which, in turn, drives excitation coil 8 to provide appropriate vibration to vane 6.

Coil driver 18 provides enough power gain for the output of the loop gain and control circuit 16 to drive the excitation coil 8. Coil driver 18 also provides a fixed gain of approximately 11 to help make up for losses in probe 4. Furthermore, coil driver 18 provides a balanced output to minimize interference with other systems and also provides a low pass filter characteristic which prevents the excitation of resonant frequencies outside the range of interest. The output impedance of coil driver 18 is low so that cable loading effects will not affect the system operation.

Both the densitometer preamplifier cable compensation circuit 12 and coil driver 18 may be located remotely from the fuel tank 2. This is because the output signal of sensor coil 10 is relatively immune to degradation due to cabling effects.

FIG. 2 illustrates more details of the presently preferred embodiment. The output signal from sensor coil 10 is provided to densitometer preamplifier 12 through cable 14. The center conductor of cable 14 is preferably connected to the inverting input of an operational amplifier U1 through a summing junction 17. The shield conductor of cable 14 is coupled to both the noninverting input of U1 and to ground. Since the operation of op-amp U1 is to keep summing junction 17 at the same potential as the non-inverting input, and since the non-inverting input is kept at ground potential, the net result is that the center conductor of cable 14 carrying the probe output signal is held at ground potential. With the center conductor at ground potential, there is no voltage across any stray resistance or capacitance to ground on the return wire from sensor coil 10. Since there is no voltage across these stray elements, no current flows through them. With no current flow, the cable strays cannot effect the system phase or gain. Thus, the system is independent of cabling effects, and the cable can be made as long as desired.

With the center conductor of cable 14 held at ground potential, the output signal from sensor coil 10 is a current. Thus, the probe output signal carried on cable 14 is current-varying and not voltage-varying. The feedback action of the op-amp U1 causes the input current to flow through feedback resistor R1. Current in resistor R1 results in an output voltage proportional to the input current provided by the sensor coil 10. Thus, the voltage invariant probe output signal carried on cable 14 is converted to a voltage varying signal at the output of preamplifier 12. Therefore, an effective measure of the density of fuel in fuel tank 2 may be provided without regard to the effects or length of cabling 14.

Op-Amp U1 amplifies the output signal from probe 4 with a phase shift relatively independent of a length or capacitance loading of the probe output cable 14. This is because Op-Amp U1 has a low input impedance. Therefore the capacitance load on the probe output cable 14 does not change the phase. Thus, the length and capacitance loading of the cable output 14 does not affect the phase of the signal provided at the output of preamplifier 12.

The output of op-amp U1 is provided to loop gain and control circuit 16. Preferably, loop gain and control circuit 16 comprises two variable gain stages composed of amplifiers U2 and U3 for controlling the loop gain. Both stages are identical and comprise a feedback loop in the form of a T attenuator which controls gain. The ground leg of the T is partially formed by the drain-source leg of a JFET transistor (Q1 and Q2). By changing the gate voltage of the JFET transistor, the drain-source resistance is modulated, thus forming a voltage-controlled T attenuator which controls gain. The gate voltage for each JFET transistor Q1 and Q2 is derived by amplifier U7, which samples the drive signals provided by coil driver 18 to the excitation coil 8. These signals are rectified by diode CR 1 and low passed filtered by capacitor C11 and resistor R29 to give a DC signal proportional to the sense coil drive. If there is no signal present at the output, the DC voltage is zero, which modulates the drain-source resistance of transistors Q1 and Q2 to a minimum value, and sets the loop gain to a maximum. As oscillations build up in the closed resonant system, the DC voltage on the gates of transistors Q1 and Q2 goes negative, causing an increase in drain-source resistance, and a decrease in the gain of amplifiers U2 and U3. The gain stabilizes at a value such that the drive to the excitation coil is approximately 1 volt peak-to-peak.

The phase of the circuit is preadjusted by component selection at installation of the densitometer equipment. Briefly, the circuit is turned depending upon the particular amplifiers used in preamplifier 12, loop gain and control circuit 16 and coil driver 18. In FIG. 2, capacitor C2 may be specially preselected in order to control the phase of the circuit. Capacitor C2 can be chosen by taking the loop circuit output and plotting phase verses frequency. Then, capacitor C2 is selected to ensure a substantially zero degree phase shift in the loop circuit. Changes in capacitors C3 and C7 in coil driver 18 may also affect the phase of the circuit. Again, empirically tuning the circuit may require substitutions in capacitors C3 and C7. Thus, the present invention can be pre-tuned by part substitution with the amplifiers or capacitors of the loop gain and control circuit 16 and coil driver 18. All such part substitutions are to be included within the scope of the appended claims.

The output of loop gain and control circuit 16 is provided in coil driver 18 to a balanced output driver U5 which provies a positive drive output on line 24 to excitation coil 8 and amplifier U7. The output signal of loop gain and control circuit 16 is also applied in parallel to a unity gain inverter stage U4 which provides an inverted signal output to standard active filter U6. Driver U6 develops on line 26 the negative phase of the balanced drive output to excitation coil 8 and amplifier U7. Both balanced output drivers U5 and U6 are standard active filters configured as 3 dB Chebyshev low pass filters. The filtered output signals from filters U5 and U6 are returned to excitation coil 8 which then properly drives vane 6 at resonance.

While the circuit of FIG. 2 is a detailed schematic of a preferred embodiment, those of skill in this field will readily appreciate that many alternative circuits may be designed depending upon the particular use to which the sensor probe is put. All such alternative circuits are to be included within the scope of protection afforded to the present invention.

Thus, what has been described is densitometer apparatus for making the probe output signal immune to cabling effects, thereby allowing signal conditioning circuitry to be located remotely from the sensor probe. Where a plurality of probes are utilized in a single system, appropriate signal conditioning circuitry may be unified in one package, for example, co-located with processor and indicator devices.

While the present invention has been described in connection with what is presently considered to be the most practical and preferred embodiment, it is to be understood that the invention is not to be limited to the disclosed embodiment. On the contrary, the present invention is intended to cover various modifications and equivalent arrangements included within the spirit and scope of the appended claims, which scope is to be accorded the broadest interpretation so as to encompass all such modifications and equivalent structures.

What the claim is:

1. Apparatus for use with a densitometer having a probe the probe having a probe output connected to a probe output cable having a signal conductor and a shield conductor, and a probe driver coupled to said probe, comprising:
   a loop circuit coupled between said probe output and said probe driver;
   amplifying means, coupled in said loop circuit, for amplifying a signal provided on said signal conductor with a phase shift independent of a length or capacitance loading of said probe output cable, said amplifying means including means for holding the signal provided on said signal conductor at ground potential as a current-varying signal; and
   phase/gain control means, coupled in said loop circuit between said amplifying means and said probe driver, for controlling said loop circuit to provide a loop gain of at least one and a substantially zero degree shift between said probe driver and said probe output signal.

2. Apparatus according to claim 1 wherein said probe output is a shielded cable having a shield conductor and a signal conductor, and wherein said amplifying means comprises an operational amplifier having first and second inputs, said first input being coupled to said signal conductor, said second input and said shield conductor being coupled to ground to hold said signal conductor at ground potential.

3. Apparatus according to claim 2 wherein said operational amplifier includes a summing junction coupled between said signal conductor and said first input, said summing junction being coupled to an output of said operational amplifier to cause said signal conductor to be held at ground potential to make an output signal of said probe voltage invariant.

4. Apparatus according to claim 3 wherein said operational amplifier includes a resistance coupled between said summing junction and said operational amplifier output to convert said voltage invariant signal to a voltage varying signal.

5. Apparatus according to claim 1 wherein said phase/gain control means includes first and second variable gain stages coupled in series between said amplifying means and said probe driver for providing said loop gain.

6. Apparatus according to claim 5 wherein each of said first and second variable gain stages comprises a T attenuator feedback loop having a grounded leg including a transistor for adjusting said loop gain.

7. Apparatus according to claim 6 wherein said first and second variable gain stages respectively comprise first and second amplifiers having said feedback loops respectively, said first amplifier having an input coupled to said amplifying means and an output, said second amplifier having an input coupled to said first amplifier output and an output coupled to said probe driver.

8. Apparatus according to claim 6 wherein said phase/gain control means includes a third amplifier coupled to said probe driver, for controlling a gate voltage of both said attenuator feedback loop transistors to control said loop gain.

9. Apparatus for use with a densitometer having a probe with an output and a probe driver coupled to said probe, comprising:
cable means, coupled to said probe output, for carrying an output signal from said probe; and
amplifier-phase/gain control means, coupled between said cable means and said probe driver, for amplifying said probe output signal and maintaining the relative phase shift thereof independently of a length or capacitance loading of said cable means, said amplifier-phase/gain control means holding said probe output signal at ground potential as a current-varying signal.

10. Apparatus according to claim 9 wherein said cable includes first and second conductors, and wherein said amplifier-phase/gain control means includes an op-amp having a first input coupled to said first conductor and a second input coupled to ground and said second conductor to hold said first conductor at ground potential so that said output signal is voltage invariant.

11. Apparatus according to claim 10 wherein said op-amp includes an output and a feedback path coupled between said op-amp output and said first conductor to cause said first conductor to be held at ground potential.

12. Apparatus according to claim 11 wherein said feedback path includes a capacitance and a resistance coupled in parallel to cause said voltage invariant signal to be voltage varying.

13. Apparatus for use with a densitometer having a probe with first and second inputs and an output, comprising:
shielded cable means having first and second conductors for carrying a signal from said probe output;
a loop circuit coupling said shielded cable means to said probe inputs; and
amplifier-phase/gain control means, coupled in said loop circuit, for providing said loop circuit with a gain factor of at least one, and for providing a substantially zero degree phase shift between said probe output and inputs, and for holding said probe output signal at ground potential as a current-varying signal.

14. Apparatus according to claim 13 wherein said amplifier-phase/gain control means includes an op-amp having an output, a feedback path, a first input coupled to said first conductor, and a second input coupled to said second conductor and ground to cause said probe signal to be held at ground potential and vary in current.

15. Apparatus according to claim 14 wherein said feedback path includes means for changing the current varying probe signal into a voltage varying signal.

16. Apparatus according to claim 14 wherein said amplifier-phase/gain control means includes an op-amp having:
a first input coupled to said first conductor;
a second input coupled to said second conductor and to ground to hold said probe signal at ground potential;
an output;
a feedback path coupled between said op-amp first input and output; and
a resistance coupled in said op-amp feedback path to convert said ground potential probe signal to a voltage-varying signal.

17. Apparatus according to claim 14 further including a probe driver means for driving said probe, said probe driver means having an input coupled to an output of said amplifier-phase/gain control means, and first and second outputs respectively coupled to said probe first and second inputs.

18. Apparatus according to claim 17 wherein said amplifier-phase/gain control means comprises:
a first amplifier having an input coupled to said op-amp output, a first feedback path, and an output;
a second amplifier having an input coupled to said first amplifier output, a second feedback path, and an output coupled to said probe driver means for driving said probe; and
a third amplifier having first and second inputs respectively coupled to said probe driver first and second outputs, and an output coupled to said first and second feedback paths for controlling said loop gain.

19. Apparatus according to claim 17 wherein said probe driver means comprises:
unity gain inverter means for inverting a gain of said amplifier-phase/gain control means output;
first low pass filter means, coupled to said amplifier-phase/gain control means output, for providing a positive drive output to said probe driver first output; and
second low pass filter means, coupled to said unity gain inverter, for providing a negative drive output to said probe driver second output.

* * * * *